(12) United States Patent
Bennett et al.

(10) Patent No.: US 7,622,455 B2
(45) Date of Patent: *Nov. 24, 2009

(54) METHODS FOR SLOWING FAMILIAL ALS DISEASE PROGRESSION

(75) Inventors: C. Frank Bennett, Carlsbad, CA (US); Susan M. Freier, San Diego, CA (US); Thomas P. Condon, Singapore (SG)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/526,134

(22) Filed: Sep. 21, 2006

(65) Prior Publication Data

US 2007/0117772 A1  May 24, 2007

Related U.S. Application Data

(63) Continuation-in-part of application No. 11/449,446, filed on Jun. 7, 2006, which is a continuation of application No. 10/672,866, filed on Sep. 26, 2003, now abandoned, which is a continuation-in-part of application No. 10/633,843, filed on Aug. 4, 2003, now Pat. No. 7,132,530, which is a continuation of application No. 09/888,360, filed on Jun. 21, 2001, now abandoned.

(60) Provisional application No. 60/719,936, filed on Sep. 21, 2005.

(51) Int. Cl.
*A61K 48/00* (2006.01)

(52) U.S. Cl. ............... 514/44; 536/24.31; 536/24.1; 536/24.5; 435/325; 435/375

(58) Field of Classification Search .............. None
See application file for complete search history.

(56) References Cited

U.S. PATENT DOCUMENTS

| | | | |
|---|---|---|---|
| 5,536,638 | A | 7/1996 | Rossau et al. |
| 5,801,154 | A | 9/1998 | Baracchini et al. |
| 5,843,641 | A | 12/1998 | Brown et al. |
| 5,849,290 | A | 12/1998 | Brown et al. |
| 5,994,076 | A | 11/1999 | Chenchik et al. |
| 5,998,148 | A | 12/1999 | Bennett et al. |
| 6,077,833 | A | 6/2000 | Bennett et al. |
| 6,194,150 | B1 | 2/2001 | Stinchcomb et al. |
| 6,352,829 | B1 | 3/2002 | Chenchik et al. |
| 6,582,908 | B2 | 6/2003 | Fodor et al. |
| 6,784,290 | B1 | 8/2004 | Monia et al. |
| 7,132,530 | B2 * | 11/2006 | Bennett et al. ............. 536/24.5 |
| 2001/0053519 | A1 | 12/2001 | Fodor et al. |
| 2002/0156040 | A1 | 10/2002 | Oberley et al. |
| 2005/0019915 | A1 | 1/2005 | Bennett et al. |
| 2006/0229268 | A1 | 10/2006 | Benjamin et al. |
| 2006/0293269 | A1 | 12/2006 | Bennett et al. |
| 2007/0054869 | A1 | 3/2007 | Bennett et al. |
| 2007/0117772 | A1 | 5/2007 | Bennett et al. |

FOREIGN PATENT DOCUMENTS

| | | |
|---|---|---|
| WO | 9005181 A1 | 5/1990 |
| WO | 9419493 A1 | 9/1994 |
| WO | 9726270 A2 | 7/1997 |
| WO | 9731012 A1 | 8/1997 |
| WO | 0203979 A2 | 1/2002 |
| WO | 02044321 A2 | 6/2002 |
| WO | 03004602 A2 | 1/2003 |
| WO | WO 03/000707 A3 | 1/2003 |
| WO | WO 2005/040180 A3 | 6/2005 |

OTHER PUBLICATIONS

Braasch et al. Novel Antisense and Peptide Nucleic Acid Strategies for Controlling Gene Expression. Biochemistry 2002, Vo. 41(14): 4503-4510.*
Scanlon, K. Anti-Genes: siRNA, Riboyzmes and Antisense. Current Pharmaceutical Biotechnology 2004, No. 5: 415-420.*
Non-final Office Action from U.S. Appl. No. 10/672,866, mail date May 3, 2005.
Non-final Office Action from U.S. Appl. No. 09/888,360, mail date May 21, 2002.
Final Rejection from U.S. Appl. No. 09/888,360, mail date Feb. 11, 2003.
Non-final Office Action from U.S. Appl. No. 10/633,843, mail date Nov. 15, 2005.
Final Rejection from U.S. Appl. No. 10/633,843, mail date Apr. 5, 2006.
Notice of Allowance from U.S. Appl. No. 10/633,843, mail date Jul. 3, 2006.
Non-final Office Action from U.S. Appl. No. 11/449,207, mail date Feb. 12, 2007.
Agrawal, S. et al., "Antisense therapeutics: is it as simple as complementary base recognition?" Mol. Med. Today (2000) 6:72-81.
Al-Chalabi, A. et al., "Recent advances in amyotrophic lateral sclerosis," Curr. Opin. Neurol. (2000) 13:397-405.
Alisky, J. M. et al., "Gene Therapy for Amyotrophic Lateral Sclerosis and Other Motor Neuron Diseases," Human Gene Therapy (2000) 11:2315-2329.
Berger, M. et al., "Universal bases for hybridization, replication and chain termination," Nucleic Acids Research (2000) 28(15):2911-2914.
Branch, A. D., "A good antisense molecule is hard to find," TIBS (1998) 23:45-50.
Brooks, B. R. et al., "El Escorial revisited: Revised criteria for the diagnosis of amyotrophic lateral sclerosis," ALS and other motor neuron disorders (2000) 1:293-299.
Bruijn, L. I. et al., "Aggregation and Motor Neuron Toxicity of an ALS-Linked SOD1 Mutant Independent from Wild-Type SOD1," Science (1998) 281:1851-1854.
Cleveland, D. W. et al., "Oxidation versus aggregation—how do SOD1 mutants cause ALS?" Nature Medicine (2000) 6(12):1320-1321.

(Continued)

*Primary Examiner*—Kimberly Chong
(74) *Attorney, Agent, or Firm*—Jones Day

(57) ABSTRACT

Methods for slowing disease progression in an individual suffering from familial ALS are provided. Also provided are methods of increasing the survival time of an individual suffering from familial ALS. These methods employ antisense oligonucleotides targeted to SOD1, for use in inhibiting the expression of SOD1 in the central nervous system of an individual suffering from familial ALS.

20 Claims, No Drawings

OTHER PUBLICATIONS

Crooke, S. T., "Basic Principles of Antisense Therapeutics," Antisense Research and Application (1998) Springer-Verlag, New York, pp. 1-50.

Fridovich, I., "Superoxide Radical and Superoxide Dismutases," Annu. Rev. Biochem. (1995) 64:97-112.

Green, D. W. et al., "Antisense Oligonucleotides: An Evolving Technology for the Modulation of Gene Expression in Human Disease," J. Am. Coll. Surg. (2000) 191(1):93-105.

Grzanna, R. et al., "Intrastriatal and intraventricular injections of oligodeoxynucleotides in the rat brain: tissue penetration, intracellular distribution and c-fos antisense effects," Molecular Brain Research (1998) 63:35-52.

Gulesserian, T. et al., "Superoxide Dismutase SOD1, Encoded on Chromosome 21, but not SOD2 is Overexpressed in Brains of Patients with Down Syndrome," J. Investig. Med. (2001) 49:41-46.

Hammond, S. M. et al., "Post-Transcriptional Gene Silencing by Double-Stranded RNA," Nature (2001) 2:110-119.

Hottinger, A. F. et al., "The Copper Chelator d-Penicillamine Delays Onset of Disease and Extends Survival in a Transgenic Mouse Model of Familial Amyotrophic Lateral Sclerosis," Eur. J. Neurosci. (1997) 9:1548-1551.

Huang, P. et al., "Superoxide dismutase as a target for the selective killing of cancer cells," Nature (2000) 407:390-395.

Jen, K.-Y. et al., "Suppression of Gene Expression by Targeted Disruption of Messenger RNA: Available Options and Current Strategies," Stem Cells (2000) 18:307-319.

Kawata, A. et al., "Aberrant splicing of human Cu/Zn superoxide dismutase (SOD1) RNA transcripts," NeuroReport (2000) 11:2649-2653.

Klivenyi, P. et al., "Neuroprotective effects of creatine in a transgenic animal model of amyotrophic lateral sclerosis," Nature Medicine (1999) 5(3):347-350.

Lee W. G. et al. "Molecular Cloning and High-Level Expression of Human Cytoplasmic Superoxide Dismutase Gene in *Escherichia coli*," Kor. J. Microbiol. (1990) 28(2):91-97.

Milner, N. et al., "Selective effective antisense reagents on combinatorial oligonucleotide arrays," Nature Biotechnology (1997) 15:537-541.

Misra, A. et al., "Drug delivery to the central nervous system: a review," J. Phar. Pharmaceut. Sci. (2003) 6 (2):6384-6387.

Muramatsu, H. et al., "Superoxide Dismutase in SAS Human Tongue Carcinoma Cell Line is a Factor Defining Invasiveness and Cell Motility," Cancer Research (1995) 55:6210-6214.

Rothstein, J. D. et al., "Chronic inhibition of superoxide dismutase produces apoptotic death of spinal neurons," Proc. Natl. Acad. Sci. USA (1994) 91:4155-4159.

Rowland, L. P., "Six important themes in amyotrophic lateral sclerosis (ALS) research, 1999," J. Neurol. Sci. (2000) 180:2-6.

Sanghvi, Y. S., "Heterocyclic Base Modifications in Nucleic Acids and Their Applications in Antisense Oligonucleotides," Antisense Research and Applications (1993) CRC Press, Boca Raton, pp. 276-278.

Skerra, A., "Phosphorothioate primers improve the amplification of DNA sequences by DNA polymerases with proofreading activity," Nucleic Acids Research (1992) 20(14):3551-3554.

Trotti, D. et al., "SOD1 mutants linked to amyotrophic lateral sclerosis selectively inactivate a glial glutamate transporter," Nature Neuroscience (1999) 2(5):427-433.

Troy, C. M. et al., "Down-regulation of copper/zinc superoxide dismutase causes apoptotic death in PC12 neuronal cells," Proc. Natl. Acad. Sci. USA (1994) 91:6384-6387.

Troy, C. M. et al., "Downregulation of Cu/Zn Superoxide Dismutase Leads to Cell Death via the Nitric Oxide-Peroxynitrite Pathway," J. Neurosci. (1996) 16(1):253-261.

Dean et al. Antisense oligonucleotide-based therapeutics for cancer. Oncogene, 2003 vol. 22:9087-9096.

Berger, I., et al., "Crystal structures of B-DNA with incorporated 2'-deoxy-2'-fluoro-arabino-furanosyl thymines: implications of conformational preorganization for duplex stability," Nucleic Acids Res. (1998) 26(10):2473-80.

Dean et al., "Antisense Oligonucleotide-based Therapeutics for Cancer," Oncogene (2003) 22:9087-9096.

Klug et al. European Journal of Physiology. (2001) 441(6): R205. Abstract No. P20-7.

PCT International Search Report for PCT/US2004/031673 dated Aug. 22, 2005.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

Kagiyama et al. (Brain Research, 1999 vol. 829:120-124).

New England BioLabs, Inc. Catalogue (1998): 121,284.

Reynolds et al., Rational siRNA design for RNA interference, Mar. 2004, Nature Biotechnology, vol. 22: 326-330.

Sinnayah et al. (Molecular Brain Research, 1997 vol. 50:43-50).

Smith et al., Journal of Clinical Investigation, 2006 vol. 116: 2290-2296.

Amorfix Life Sciences Ltd. "Amorfix Life Sciences Discovers Common Link Between ALS and Alzheimer's Disease" Press Release, Nov. 27, 2007.

PCT International Search Report for PCT/US2002/19664 dated Jan. 14, 2003.

Partial European Search Report for Application EP 02742241 dated Nov. 8, 2004.

Office Action for U.S. Appl. No. 11/449,446 dated Jul. 20, 2007.
Final Rejection for U.S. Appl. No. 11/449,446 dated Jan. 4, 2008.
Office Action for U.S. Appl. No. 11/449,446 dated Jun. 6, 2008.
Final Rejection for U.S. Appl. No. 11/449,446 dated Feb. 23, 2009.
Final Rejection for U.S. Appl. No. 10/672,866 dated Mar. 7, 2006.
Notice of Allowance for U.S. Appl. No. 11/449,207 (filed on Jun. 07, 2006) dated Aug. 6, 2009.
Non-final Office Action for U.S. Appl. No. 11/449,446 (filed on Jun. 07, 2006) dated Aug. 11, 2009.

\* cited by examiner

METHODS FOR SLOWING FAMILIAL ALS DISEASE PROGRESSION

RELATED APPLICATIONS

This application is a continuation-in-part of U.S. application Ser. No. 11/449,446, filed Jun. 7, 2006, which is a continuation of U.S. application Ser. No 10/672,866, filed Sep. 26, 2003, which is a continuation-in-part of U.S application Ser. No. 10/633,843, filed Aug. 4, 2003, which is a continuation of U.S. application Ser. No. 09/888,360, filed Jun. 21, 2001. Further, this application claims priority under 35 U.S.C. § 119(e) to U.S. Provisional Application Ser. No. 60/719,936, filed Sep. 21, 2005. The entire contents of these documents are incorporated herein by reference.

FIELD OF THE INVENTION

The present invention provides compositions and methods for slowing disease progression in an individual suffering from familial amyotrophic lateral sclerosis. In particular, this invention relates to antisense compounds, particularly antisense oligonucleotides, complementary to SOD1 nucleic acids. Such antisense oligonucleotides have been shown to inhibit the expression of SOD1.

BACKGROUND OF THE INVENTION

The superoxide anion ($O_2^-$) is a potentially harmful cellular by-product produced primarily by errors of oxidative phosphorylation in mitochondria (Cleveland and Liu, Nat. Med., 2000, 6, 1320-1321). Some of the targets for oxidation by superoxide in biological systems include the iron-sulfur dehydratases, aconitase and fumarases. Release of Fe (II) from these superoxide-inactivated enzymes results in Fenton-type production of hydroxyl radicals which are capable of attacking virtually any cellular target, most notably DNA (Fridovich, Annu. Rev. Biochem., 1995, 64, 97-112).

The enzymes known as the superoxide dismutases (SODs) provide defense against oxidative damage of biomolecules by catalyzing the dismutation of superoxide to hydrogen peroxide ($H_2O_2$) (Fridovich, Annu. Rev. Biochem., 1995, 64, 97-112). Two major classes of superoxide dismutases exist. One consists of a group of enzymes with active sites containing copper and zinc while the other class has either manganese or iron at the active site (Fridovich, Annu. Rev. Biochem., 1995, 64, 97-112).

The soluble superoxide dismutase 1 enzyme (also known as SOD1 and Cu/Zn superoxide dismutase) contains a zinc- and copper-type active site (Fridovich, Annu. Rev. Biochem., 1995, 64, 97-112). Lee et al. reported the molecular cloning and high-level expression of human cytoplasmic superoxide dismutase gene in E. coli in 1990 (Lee et al., Misaengmul Hakhoechi, 1990, 28, 91-97). Studies of transgenic mice carrying a mutant human superoxide dismutase 1 gene, for example, transgenic mice expressing a human SOD1 gene bearing glycine 93 to alanine (G93A) mutation.

Mutations in the superoxide dismutase 1 gene are associated with a dominantly-inherited form of amyotrophic lateral sclerosis (ALS, also known as Lou Gehrig's disease) a disorder characterized by a selective degeneration of upper and lower motor neurons (Cleveland and Liu, Nat. Med., 2000, 6, 1320-1321). The deleterious effects of various mutations on superoxide dismutase 1 are most likely mediated through a gain of toxic function rather than a loss of superoxide dismutase 1 activity, as the complete absence of superoxide dismutase 1 in mice neither diminishes life nor provokes overt disease (Al-Chalabi and Leigh, Curr. Opin. Neurol., 2000, 13, 397-405; Alisky and Davidson, Hum. Gene Ther., 2000, 11, 2315-2329).

Cleveland and Liu proposed two models for mutant superoxide dismutase 1 toxicity (Cleveland and Liu, Nat. Med., 2000, 6, 1320-1321). The "oxidative hypothesis" ascribes toxicity to binding of aberrant substrates such as peroxynitrite or hydrogen peroxide which gain access to the catalytic copper ion through mutation-dependent loosening of the native superoxide dismutase 1 protein conformation (Cleveland and Liu, Nat. Med., 2000, 6, 1320-1321). A second possible mechanism for mutant superoxide dismutase 1 toxicity involves the misfolding and aggregation of mutant superoxide dismutase 1 proteins (Cleveland and Liu, Nat. Med., 2000, 6, 1320-1321). The idea that aggregates contribute to ALS has received major support from the observation that murine models of superoxide dismutase 1 mutant-mediated disease feature prominent intracellular inclusions in motor neurons and, in some cases, in the astrocytes surrounding them as well (Bruijn et al., Science, 1998, 281, 1851-1854). Furthermore, Bruijn et al. also demonstrate that neither elimination nor elevation of wild-type superoxide dismutase 1 was found to affect disease induced by mutant superoxide dismutase 1 in mice (Bruijn et al., Science, 1998, 281, 1851-1854).

Riluzole, a glutamate regulatory drug, is approved for use in ALS patients in some countries, but has only a modest effect on survival. Accordingly, there remains an unmet need for therapeutic regimens that slow familial ALS disease progression and increase survival of familial ALS patients.

SUMMARY OF THE INVENTION

The present invention provides methods of slowing disease progression in an individual suffering from familial amyotrophic lateral sclerosis (ALS), comprising administering to the individual a therapeutically effective amount of a pharmaceutical composition comprising an antisense oligonucleotide 17 to 25 nucleobases in length complementary to nucleobases 66 to 102 of SEQ ID NO: 1, thereby slowing disease progression. The administering may comprise delivery to the cerebrospinal fluid of the individual, and may further comprise intrathecal infusion. A slowing of disease progression is measured by an improvement in one or more indicators of ALS disease progression selected from ALS-FRS-R, $FEV_1$, FVC, or muscle strength measurements. The methods further comprise increasing the survival time of an individual suffering from familial ALS.

The methods provided herein comprise the administration of an antisense oligonucleotide complementary to nucleobases 83 to 102 of SEQ ID NO: 1. The antisense oligonucleotide may be fully complementary to nucleotides 83 to 102 of SEQ ID NO: 1. Further, the antisense oligonucleotide may consist essentially of ISIS 333611. Additionally, the antisense oligonucleotide may consist of ISIS 333611.

The antisense oligonucleotides employed in the methods provided herein comprise at least one modified internucleoside linkage, such as a phosphorothioate internucleoside linkage, a modified sugar moiety, such as a 2'-O-methoxyethyl sugar moiety or a bicyclic nucleic acid sugar moiety, or a modified nucleobase, such as a 5-methylcytosine.

The present invention provides methods of slowing disease progression in an individual suffering from familial ALS comprising administering an antisense oligonucleotide that is a chimeric oligonucleotide. The chimeric oligonucleotide comprises a 2'-deoxynucleotide gap segment positioned between 5' and 3' wing segments. The wing segments are comprised of nucleosides containing a sugar moiety selected from a 2'-O-methoxyethyl sugar moiety or a bicyclic nucleic acid sugar moiety. The gap segment may be ten 2'-deoxynucleotides in length and each of the wing segments may be five 2'-O-methoxyethyl nucleotides in length. The chimeric oligonucleotide may be uniformly comprised of phosphorthioate internucleoside linkages. Further, each cytosine of the chimeric oligonucleotide may be a 5'-methylcytosine.

Further provided are methods comprising selecting an individual who has received a diagnosis of familial amyotrophic lateral sclerosis (ALS), administering to the individual a therapeutically effective amount of a pharmaceutical composition comprising an antisense oligonucleotide 17 to 25 nucleobases in length complementary to nucleobases 66 to 102 of SEQ ID NO: 1, and monitoring ALS disease progression in the individual.

DETAILED DESCRIPTION OF THE INVENTION

Over 100 mutations of the human SOD1 gene have been identified, and altogether account for approximately 20% of familial amyotrophic lateral sclerosis (ALS) cases. Some mutations, such as the A4V mutation most commonly found in the United States, are highly lethal and result in survival only nine months from the onset of disease symptoms. Other mutations of SOD1 manifest in a slower disease course.

It has been discovered that antisense inhibition of superoxide dismutase 1 (SOD1) in an animal model of familial ALS reduces both SOD1 mRNA and protein, and further results in a slowing of disease progression and, importantly, increased survival time. Accordingly, the present invention provides methods for the slowing of disease progression in an individual suffering from familial ALS by delivering to the cerebrospinal fluid of the individual a therapeutically effective amount of a pharmaceutical composition comprising an antisense oligonucleotide targeted to SOD1. Such methods further comprise increasing survival time of an individual suffering from familial ALS. Slowing of disease progression is indicated by an improvement in one or more indicators of ALS disease progression, including, without limitation, the revised ALS functional rating scale, pulmonary function tests, and muscle strength measurements.

The present invention employs antisense compounds, particularly antisense oligonucleotides, for use in modulating the function of nucleic acid molecules encoding SOD1, ultimately modulating the amount of SOD1 protein produced. This is accomplished by providing antisense oligonucleotides which hybridize to and inhibit the expression of one or more nucleic acids encoding SOD1. Such antisense oligonucleotides are considered to be "targeted to SOD1." Antisense oligonucleotides of the present invention do not necessarily distinguish between wild-type SOD1 mRNA and SOD1 mRNAs bearing mutations. While an object of the present invention is to reduce SOD1 mRNAs bearing mutations, the conconmitant reduction of wild-type SOD1 appear to be safe, as reductions or complete loss of SOD1 does not produce overt disease or compromise life span in experimental animal models.

In certain embodiments, an antisense oligonucleotide targeted to SOD1 is complementary to nucleobases 66 to 102 of a nucleic acid molecule encoding SOD1 (GENBANK® accession no. X02317.1, incorporated herein as SEQ ID NO: 1). In additional embodiments, an antisense oligonucleotide targeted to SOD1 is complementary to nucleotides 83 to 102 of SEQ ID NO: 1. In preferred embodiments, an antisense oligonucleotide targeted to SOD1 is fully complementary to nucleotides 83 to 102 of SEQ ID NO: 1. In further preferred embodiments, the antisense oligonucleotide is ISIS 333611.

As used herein, an "individual suffering from familial ALS" is an individual who has received from a health professional, such as a physician, a diagnosis of familial ALS. Relevant diagnostic tests are well known in the art and are understood to include, without limitation, genetic testing to determine the presence of a mutation in the SOD1 gene, neurological examination, and the El Escorial criteria (see, for example, Brooks et al., *Amyothoph. Lateral Scler. other Motor Neuron Disorders*, 2000, 293-299). An "individual prone to familial ALS" is understood to include an individual who, based on a physician's assessment, is not yet suffering from familial ALS but is likely to develop familial ALS.

In order for antisense inhibition of SOD1 to have a clinically desirable effect on familial ALS progression, it is beneficial to deliver an antisense oligonucleotide targeted to SOD1 to the central nervous system (CNS) of an individual suffering from familial ALS, and in particular to the regions of the CNS affected by familial ALS. As the blood-brain barrier is generally impermeable to antisense oligonucleotides administered systemically, a preferred method of providing antisense oligonucleotides targeted to SOD1 to the tissues of the CNS is via administration of the antisense oligonucleotides directly into the cerebrospinal fluid (CSF). As is known in the art, means for delivery to the CSF include intrathecal (IT) and intracerebroventricular (ICV) administration. As is further known in the art, IT or ICV administration may be achieved through the use of surgically implanted pumps that infuse a therapeutic agent into the cerebrospinal fluid. As used herein, "delivery to the CSF" and "administration to the CSF" encompass the IT infusion or ICV infusion of antisense oligonucleotides targeted to SOD1 through the use of an infusion pump. In some embodiments, IT infusion is a preferred means for delivery to the CSF. In preferred embodiments, the antisense oligonucleotide is continuously infused into the CSF for the entire course of treatment; such administration is referred to as "continuous infusion" or, in the case of IT infusion, "continuous IT infusion."

In the context of the present invention, a preferred means for delivery of antisense oligonucleotide to the CSF employs an infusion pump such as Medtronic SyncroMed® II pump. The SyncroMed® II pump is surgically implanted according the procedures set forth by the manufacturer. The pump contains a reservoir for retaining a drug solution, which is pumped at a programmed dose into a catheter that is surgically implanted. For intrathecal administration of a drug, the catheter is surgically intrathecally implanted. In the context of the present invention, the drug is the pharmaceutical composition comprising an antisense oligonucleotide targeted to SOD1.

As used herein, a "pharmaceutical composition comprising an antisense oligonucleotide" refers to a composition comprising an antisense oligonucleotide targeted to SOD1 in a pharmaceutically acceptable diluent. By way of example, a suitable pharmaceutically acceptable diluent is phosphate-buffered saline. In some embodiments, the pharmaceutical composition comprises an antisense oligonucleotide complementary to nucleotides 66 to 102 of SOD1 in phosphate-buffered saline. In preferred embodiments, the pharmaceutical composition comprises an antisense oligonucleotide complementary to nucleotides 83 to 102 of SEQ ID NO: 1 in phosphate-buffered saline. In further preferred embodiments, the pharmaceutical composition comprises an antisense oligonucleotide fully complementary to nucleotides 83 to 102 of SEQ ID NO: 1 in phosphate-buffered saline. In more preferred embodiments, the pharmaceutical composition comprises ISIS 333611 in phosphate-buffered saline. ISIS 333611 is the nonadecasodium salt of the antisense oligonucleotide having the nucleobase sequence CCGTCGCCCT-TCAGCACGCA (SEQ ID NO: 2), where nucleosides 1 to 5 and 16 to 20 have 2'-O-methoxyethyl sugar moieties, nucleosides 6 to 15 are 2'-deoxynucleotides, each internucleoside linkage is a phosphorothioate linkage, and each cytosine is a 5-methylcytosine.

As used herein, a "therapeutically effective amount" is an amount of an antisense oligonucleotide targeted to SOD1 required to produce a slowing of disease progression and/or an increase in survival time in an individual suffering from familial ALS. Accordingly, a therapeutically effect amount is an amount that will result in an improvement in one or more indicators of ALS progression, such as, for example, the revised ALSFSR, $FEV_1$, FCV, and muscle strength measurements. In some embodiments, a therapeutically effective amount of an antisense oligonucleotide targeted to SOD1 ranges from 8 mg to 12 mg of antisense oligonucleotide. In preferred embodiments, a therapeutically effect amount of an antisense oligonucleotide targeted to SOD1 is 10 mg. In one embodiment, a therapeutically effective amount of an antisense oligonucleotide targeted to SOD1 is administered via continuous infusion for a minimum of 28 days. In preferred embodiments, antisense oligonucleotide is delivered via IT infusion. In further preferred embodiments, the antisense oligonucleotide administered is ISIS 333611.

As used herein, "slowing disease progression" means the prevention of a clinically undesirable change in one or more disabilities in an individual suffering from familial ALS, and is assessed by methods routinely practiced in the art, for example, the revised ALSFSR, pulmonary function tests, and muscle strength measurements. Such methods are herein referred to as "indicators of ALS disease progression."

As used herein, an "improvement in a indicator of ALS disease progression" refers to slowing of the rate of change in one or more of the indicators of ALS disease progression described herein. An improvement in an indicator of ALS disease progression further includes a lack of a measurable change in one or more of the indicators of ALS disease progression described herein. An improvement in an indicator of ALS disease progression additionally includes a positive change in one of the indicators of ALS disease progression described herein, such as, for example, an increase in an ALSFSR-R score. One of skill in the art will appreciate that is well within the abilities of a physician to identify a slowing of disease progression in an individual suffering from familial ALS, using one or more of the disease assessment tests described herein. Additionally, it is understood that a physician may administer to the individual diagnostic tests other than those described herein, such as additional pulmonary function tests or muscle strength measurement tests, to assess the rate of disease progression in an individual suffering from familial ALS.

A slowing of disease progression may further comprise an "increase in survival time" in an individual suffering from familial ALS. It is understood that a physician can use one or more of the disease assessment tests described herein to predict an approximate survival time of an individual suffering from familial ALS. A physician may additionally use the known disease course of a particular familial ALS mutation to predict survival time.

The "revised ALS functional rating scale" or "ALSFRS-R" is routinely used by physicians and is a validated rating instrument for monitoring the progression of disability in ALS patients. The ALSFRS-R includes 12 questions that ask a physician to rate his or her impression of an ALS patient's level of functional impairment in performing one of ten common tasks, for example, climbing stairs. Each task is rated on a five-point scale, where a score of zero indicates an inability to perform a task and a score of four indicates normal ability in performing a task. Individual item scores are summed to produce a reported score of between zero (worst) and 48 (best).

ALS eventually results in progressive muscle weakness. Pulmonary function tests (PFTs) are employed to reveal the extent and progression respiratory muscle weakness. Pulmonary function tests include measurements of the "forced expiratory volume in one second" ($FEV_1$), which is the amount of air than an individual can forcefully exhale during the first second of exhalation following inhalation, as well as measurements of "forced vital capacity" (FVC), which is the total amount of air that an individual can forcefully exhale following inhalation. $FEV_1$ and FVC are typically reduced in individuals with neuromuscular diseases, such as ALS. Pulmonary function tests may be administered using instrument that directly measures the volume of air displaced during exhalation, or measures airflow during exhalation by a flow sensing device. An example of such an instrument is a spirometer. ALS disease progression is also evaluated by assessing the extent and progression of whole body muscle weakness. Muscle strength measurements, include, but are not limited to, hand held dynamometry, maximum voluntary isometric contraction (MVIC) strain gauge measurements, and manual muscle testing. Muscle strength tests routinely use an instrument that measures how much force (for example, pounds of force) an individual can apply to the instrument using a selected group of muscles, such as the hand muscles. Such an instrument includes a dynamometer.

Antisense Compounds

In the context of the present invention, the term "oligomeric compound(s)" refers to polymeric structures which are capable of hybridizing to at least a region of an RNA molecule. Generally, an oligomeric compound is "antisense" to a target nucleic acid when it comprises the reverse complement of the corresponding region of the target nucleic acid. Such oligomeric compounds are known as "antisense compounds", which include, without limitation, oligonucleotides (i.e. antisense oligonucleotides), oligonucleosides, oligonucleotide analogs, oligonucleotide mimetics and combinations of these. In general, an antisense compound comprises a backbone of linked monomeric subunits (sugar moieties) where each linked monomeric subunit is directly or indirectly attached to a heterocyclic base moiety. Modifications to antisense compounds encompass substitutions or changes to internucleoside linkages, sugar moieties, or heterocyclic base moieties, such as those described below. As used herein, the term "modification" includes substitution and/or any change from a starting or natural nucleoside or nucleotide. Modified antisense compounds are often preferred over native forms because of desirable properties such as, for example, enhanced cellular uptake, enhanced affinity for nucleic acid target, increased stability in the presence of nucleases, or increased inhibitory activity. Antisense compounds are often defined in the art to comprise the further limitation of, once hybridized to a target, being able to induce or trigger a reduction in target gene expression or target gene levels. In one embodiment, the antisense compounds, e.g. antisense oligonucleotides, trigger a reduction in the levels of a nucleic acid encoding SOD1.

"Targeting" an antisense oligonucleotide to a nucleic acid encoding SOD1 includes the determination of at least one target segment within a nucleic acid encoding SOD1 for hybridization to occur such that the desired effect, e.g., inhibition of SOD1 mRNA expression, will result. As used herein, the terms "SOD1 target nucleic acid" and "nucleic acid encoding SOD1" encompass RNA (including pre-mRNA and mRNA) transcribed from DNA encoding SOD1, and also cDNA derived from such RNA. The inhibition of gene expression that results from the hybridization of an antisense oligonucleotide with a target nucleic acid is generally referred to as "antisense inhibition". The functions of RNA to be interfered with include, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the SOD1 protein. In the context of the present invention, "modulation" means either an increase (stimulation) or a decrease (inhibition) in the expression of a gene. In the context of the present invention, inhibition is the preferred form of modulation of gene expression and SOD1 mRNA (e.g. SEQ ID NO: 1) is a preferred target.

As used herein, a "target segment" means a sequence of an SOD1 target nucleic acid to which one or more antisense oligonucleotides are complementary. Multiple antisense oligonucleotides complementary to a given target segment may or may not have overlapping sequences. Within the context of the present invention, the term "target site" is defined as a sequence of an SOD1 nucleic acid to which one antisense oligonucleotide is complementary. For example, the nucleobase sequence of ISIS 333611 is complementary to nucleobases 83 to 102 of SEQ ID NO: 1, thus these nucleobases represent a target site of an SOD1 nucleic acid. Several antisense oligonucleotides of the invention have target sites within nucleobases 66 to 102 of SEQ ID NO: 1, thus these nucleobases represent a target segment of an SOD1 nucleic acid. In some embodiments, a target segment and target site are represented by the same nucleobase sequence.

In the practice of the methods of the present invention, particularly preferred SOD1 target segments include, without limitation, nucleobases 66 to 102 of SEQ ID NO: 1; nucleobases 73 to 102 of SEQ ID NO: 1; and nucleobases 79 to 102 of SEQ ID NO: 1. Particularly preferred target sites include nucleobases 81 to 100 of SEQ ID NO: 1, to which ISIS 146145 (SEQ ID NO. 3) is complementary; and nucleobases 83 to 102 of SEQ ID NO: 1, to which ISIS 333611 (SEQ ID NO. 2) is complementary.

The antisense oligonucleotides in accordance with this invention comprise from 15 to 30 to nucleosides in length, i.e., from 15 to 30 linked nucleosides. One of skill in the art will appreciate that this embodies antisense oligonucleotides of 15, 16, 17, 18, 19, 20, 21, 22, 23, 24, 25, 26, 27, 28, 29, or 30 nucleosides in length.

In one embodiment, the antisense oligonucleotides of the invention are 17 to 25 nucleosides in length, as exemplified herein.

In preferred embodiments, the antisense oligonucleotides of the invention are 19, 20, 21, 22 or 23 nucleosides in length.

"Base complementarity" as used herein, refers to the capacity for the precise base pairing of nucleobases of an antisense oligonucleotide with corresponding nucleobases in a target nucleic acid (i.e., hybridization). In the context of the present invention, the mechanism of pairing involves hydrogen bonding, which may be Watson-Crick, Hoogsteen or reversed Hoogsteen hydrogen bonding, between corresponding nucleobases. Both natural and modified nucleobases are capable of participating in hydrogen bonding. Hybridization can occur under varying circumstances.

As used herein, an antisense oligonucleotide is "fully complementary" to a target nucleic acid when each nucleobase of the antisense oligonucleotide is capable of undergoing precise base pairing with an equal number of nucleobases in the target nucleic acid. It is understood in the art that the sequence of the antisense oligonucleotide need not be fully complementary to that of its target nucleic acid to be active in inhibiting the activity of the target nucleic acid. In some embodiments there are "non-complementary" positions, also known as "mismatches", between the antisense oligonucleotide and the target nucleic acid, and such non-complementary positions may be tolerated between an antisense oligonucleotide and the target nucleic acid provided that the antisense oligonucleotide remains specifically hybridizable to the target nucleic acid. For example, ISIS 333611, having two non-complementary nucleobases with respect to monkey SOD1, is capable of reducing monkey SOD1 mRNA levels in cultured cells. A "non-complementary nucleobase" means a nucleobase of an antisense oligonucleotide that is unable to undergo precise base pairing with a nucleobase at a corresponding position in a target nucleic acid. As used herein, the terms "non-complementary" and "mismatch" are interchangable. In the context of the present invention, antisense oligonucleotides having no more than three non-complementary nucleobases with respect to a nucleic acid encoding SOD1 are considered "complementary" to a nucleic acid encoding SOD1. In preferred embodiments, the antisense oligonucleotide contains no more than two non-complementary nucleobases with respect to a nucleic acid encoding SOD1. In further preferred embodiments, the antisense oligonucleotide contains no more than one non-complementary nucleobases with respect to a nucleic acid encoding SOD1.

The location of a non-complementary nucleobase may be at the 5' end or 3' end of the antisense oligonucleotide. Alternatively, the non-complementary nucleobase may be at an internal position in the antisense oligonucleotide. When two or more non-complementary nucleobases are present, they may be contiguous (i.e. linked) or non-contiguous.

In other embodiments of the invention, the antisense oligonucleotides comprise at least 90% sequence complementarity to an SOD1 target nucleic acid. In further embodiments of the invention, the antisense oligonucleotides comprise at least 95% sequence complementarity to an SOD1 target nucleic acid. Percent complementarity of an antisense oligonucleotide with a region of a target nucleic acid can be determined routinely by those having ordinary skill in the art, and may be accomplished using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Antisense oligonucleotides may have a defined percent identity to a SEQ ID NO, or an antisense oligonucleotide having a specific ISIS number. This identity may be over the entire length of the antisense oligonucleotide, or over less than the entire length of the antisense oligonucleotide. Calculating percent identity is well within the ability of those skilled in the art. It is understood by those skilled in the art that an antisense oligonucleotide need not have an identical sequence to those described herein to function similarly to the antisense oligonucleotides described herein. For example, antisense oligonucleotides having at least 90%, or at least 95%, identity to antisense oligonucleotides taught herein are contemplated in the present invention.

Shortened or truncated versions of antisense oligonucleotides taught herein have one, two or more nucleosides deleted, and are contemplated in the present invention. When an antisense oligonucleotide has two or more deleted nucleosides, the deleted nucleosides may be adjacent to each other, for example, in an antisense oligonucleotide having two nucleosides truncated from the 5' end (5' truncation), or alternatively from the 3' end (3' truncation), of the antisense oligonucleotide. Alternatively, the deleted nucleosides may be dispersed through out the antisense, for example, in an antisense oligonucleotide having one nucleoside deleted from the 5' end and one nucleoside deleted from the 3' end.

Also falling within the scope of the invention are lengthened versions of antisense oligonucleotides taught herein, i.e. antisense oligonucleotides having one or more additional nucleosides relative to an antisense oligonucleotide disclosed herein. When two are more additional nucleosides are present, the added nucleosides may be adjacent to each other, for example, in an antisense oligonucleotide having two nucleosides added to the 5' end (5' addition), or alternatively to the 3' end (3' addition), of the antisense oligonucleotide. Alternatively, the added nucleosides may be dispersed throughout the antisense oligonucleotide, for example, in an antisense oligonucleotide having one nucleoside added to the 5' end and one nucleoside added to the 3' end.

Antisense oligonucleotides of the invention may be also be described as complementary to a portion of a target site. A "portion" is defined as at least 18 contiguous nucleobases of a target site. In other embodiments, a portion is 19 or 20 contiguous nucleobases of a target site. By way of example, antisense oligonucleotides may be complementary, or alternatively fully complementary, to a 19 nucleobase portion of SEQ ID NO: 1.

The antisense compounds of the invention are synthesized in vitro and do not include antisense compositions of biological origin, or genetic vector constructs designed to direct the in vivo synthesis of antisense molecules.

Antisense Compound Modifications

Any of the antisense compounds taught herein, including antisense oligonucleotides taught herein, may contain modifications which confer desirable properties to the antisense compound including, but are not limited to, increased affinity of an antisense oligonucleotide for its target RNA and increased resistance to nucleases.

As is known in the art, a nucleoside is a base-sugar combination. The base (also known as nucleobase) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers generally to an oligomer or polymer of ribonucleic acid (RNA) or deoxyribonucleic acid (DNA), and may be used to refer to unmodified oligonucleotides or oligonucleotide analogs. The term "unmodified oligonucleotide" refers generally to oligonucleotides composed of naturally occuring nucleobases, sugars, and covalent internucleoside linkages. The term "oligonucleotide analog" refers to oligonucleotides that have one or more non-naturally occurring nucleobases, sugars, and/or internucleoside linkages. Such non-naturally occurring oligonucleotides are often selected over naturally occurring forms because of desirable properties such as, for example, enhanced cellular uptake, enhanced affinity for target nucleic acids, increased stability in the presence of nucleases, or increased inhibitory activity.

Chemically modified nucleosides may also be employed to increase the binding affinity of a shortened or truncated antisense compound for its target nucleic acid. Consequently, comparable results can often be obtained with shorter antisense compounds that have such chemically modified nucleosides.

Modified Internucleoside Linkages

Specific examples of antisense compounds useful in this invention include oligonucleotides containing one or more modified, i.e. non-naturally occurring, internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases.

As defined in this specification, oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. For the purposes of this specification, and as sometimes referenced in the art, modified oligonucleotides that do not have a phosphorus atom in their internucleoside backbone can also be considered to be "oligonucleosides". Methods of preparation of phosphorous-containing and non-phosphorous-containing linkages are well known to those skilled in the art.

Modified Sugar Moieties

Antisense compounds of the invention may also contain one or more nucleosides having modified sugar moieties. The base moieties (natural, modified or a combination thereof) are maintained for hybridization with an appropriate nucleic acid target. Sugar modifications may impart nuclease stability, binding affinity or some other beneficial biological property to the antisense compounds. The furanosyl sugar ring of a nucleoside can be modified in a number of ways including, but not limited to, addition of a substituent group, particularly at the 2' position, bridging of two non-geminal ring atoms to form a bicyclic nucleic acid (BNA) and substitution of an atom or group such as —S—, —N(R)— or —C($R_1$)($R_2$) for the ring oxygen at the 4'-position. A representative list of preferred modified sugars includes but is not limited to: substituted sugars, especially 2'-substituted sugars having a 2'-F, 2'-OCH$_2$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=2. Sugars can also be replaced with sugar mimetic groups. Methods for the preparations of modified sugars are well known to those skilled in the art.

Modified Nucleobases

Antisense compounds of the invention may also contain one or more nucleobase (often referred to in the art simply as "base") modifications or substitutions which are structurally distinguishable from, yet functionally interchangeable with, naturally occurring or synthetic unmodified nucleobases. Such nucleobase modifications may impart nuclease stability, binding affinity or some other beneficial biological property to the antisense compounds. As used herein, "unmodified" or "natural" nucleobases include the purine bases adenine (A)

and guanine (G), and the pyrimidine bases thymine (T), cytosine (C) and uracil (U). Modified nucleobases also referred to herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of the antisense compounds of the invention includ 5-substituted pyrimidines, 6-azapyrimidines and N-2, N-6 and O-6 substituted purines, including 2 aminopropyladenine, 5-propynyluracil and 5-propynylcytosine.

Certain nucleobase substitutions, including 5-methylcytosinse substitutions, are particularly useful for increasing the binding affinity of the oligonucleotides of the invention. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Oligonucleotide Mimetics

Antisense compounds can also include an "oligonucleotide mimetic," which refers to oligonucleotides in which only the furanose ring or both the furanose ring and the internucleoside linkage are replaced with novel groups.

As used herein the term "mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc. Acid Res. 2000, 28:2911-14, incorporated herein by reference). Methods of synthesis of sugar, nucleoside and nucleobase mimetics are well known to those skilled in the art.

Conjugated Antisense Compounds

One substitution that can be appended to the antisense compounds of the invention involves the linkage of one or more moieties or conjugates which enhance the activity, cellular distribution or cellular uptake of the resulting antisense compounds. In one embodiment such modified antisense compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of the antisense compounds. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds used in the compositions of the present invention can also be modified to have one or more stabilizing groups that are generally attached to one or both termini of antisense compounds to enhance properties such as, for example, nuclease stability. Included in stabilizing groups are cap structures. By "cap structure" or "terminal cap moiety" is meant chemical modifications, which have been incorporated at either terminus of an antisense compound (see for example Wincott et al., WO 97/26270). These terminal modifications protect the antisense compounds having terminal nucleic acid molecules from exonuclease degradation, and can help in delivery and/or localization within a cell. The cap can be present at the 5'-terminus (5'-cap), or at the 3'-terminus (3'-cap), or can be present on both termini. For double-stranded antisense compounds, the cap may be present at either or both termini of either strand. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Antisense Compound Motifs

Antisense compounds of this invention may have the chemically modified subunits arranged in patterns enhance the inhibitory activity of the antisense compounds. These patterns are described herein as "motifs."

As used in the present invention the term "gapped motif" or "gapmer" is meant to include an antisense compound having an internal region (also referred to as a "gap" or "gap segment") positioned between two external regions (also referred to as "wing" or "wing segment"). The regions are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include LNA™ or ENA™, among others). In general, each distinct region comprises uniform sugar moieties.

Gapped motifs or gapmers are further defined as being either "symmetric" or "asymmetric". A gapmer wherein the nucleosides of the first wing have the same sugar modifications as the nucleosides of the second wing is termed a symmetric gapped antisense compound. Symmetric gapmers can have, for example, an internal region comprising a first sugar moiety, and external regions each comprising a second sugar moiety, wherein at least one sugar moiety is a modified sugar moiety.

"Chimeric antisense compounds" or "chimeras," in the context of this invention, are antisense compounds that at least 2 chemically distinct regions, each made up of at least one monomer unit, i.e., a nucleotide or nucleoside in the case of a nucleic acid based antisense compound. Accordingly, antisense compounds having a gapmer motif considered chimeric antisense compounds.

Chimeric antisense compounds typically contain at least one region modified so as to confer increased resistance to nuclease degradation, increased cellular uptake, increased binding affinity for the target nucleic acid, and/or increased inhibitory activity. By way of example, an antisense compound may be designed to comprise a region that serves as a substrate for the cellular endonuclease RNase H, which cleaves the RNA strand of an RNA:DNA duplex. In the case of gapmer, the internal region generally serves as the substrate for endonuclease cleavage.

Compositions and Methods for Formulating Pharmaceutical Compositions

The antisense compounds of the invention may also be admixed with pharmaceutically acceptable substances, active and/or inert, that are well known to those skilled in the art.

The present invention also includes pharmaceutical compositions and formulations that include the antisense compounds and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The antisense compounds and compositions of the invention can be utilized in pharmaceutical compositions by adding an effective amount of the compound or composition to a suitable pharmaceutically acceptable diluent or carrier. In the context of the present invention, a pharmaceutically acceptable diluent includes phosphate-buffered saline (PBS). PBS is a diluent suitable for use in compositions to be delivered to the CNS.

The antisense compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the antisense compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. This can include the incorporation of additional nucleosides at one or both ends of an antisense compound which are cleaved by endogenous nucleases within the body, to form the active antisense compound.

The term "pharmaceutically acceptable salts" refers to physiologically and pharmaceutically acceptable salts of the antisense compounds and compositions of the invention: i.e., salts that retain the desired biological activity of the parent compound and do not impart undesired toxicological effects thereto. Suitable examples include, but are not limited to, sodium and potassium salts.

Cell Culture and Antisense Oligonucleotide Treatment

The effects of antisense oligonucleotides on the level, activity or expression of SOD1 target nucleic acids can be tested in vitro in a variety of cell types. Cell types used for such analyses are available from commerical vendors (e.g. American Type Culture Collection, Manassus, Va.; Zen-Bio, Inc., Research Triangle Park, NC; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, A549 cells, fibroblasts, and neuronal cells.

In vitro Testing of Antisense Oligonucleotides

In general, when cells reach approximately 60-80% confluency, they are treated with antisense oligonucleotides of the invention.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense compound.

Cells are treated with antisense oligonucleotides by routine methods well known to those skilled in the art. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM.

In vivo Testing of Antisense Oligonucleotides

Antisense oligonucleotides are tested in animals to assess their ability to inhibit expression of a target nucleic acid and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous, and further includes intrathecal and intracerebroventricular routes of administration. Calculation of antisense oligonucleotide dosage and dosing frequency is within the abilities of those skilled in the art, and depends upon factors such as route of administration and animal body weight. Following a period of treatment with antisense oligonucleotides, RNA is isolated from various tissues and changes in target nucleic acid expression are measured. Changes in proteins encoded by target nucleic acids may also be measured. The types of phenotypic changes selected for monitoring are dependent upon the cellular pathway and disease with which the target nucleic acid is associated.

RNA Isolation

RNA analysis can be performed on total cellular RNA or poly(A)+ mRNA.

Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an SOD1 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH, or by quantifying total RNA using RIBOGREEN® (Molecular Probes, Inc. Eugene, Oreg.). GAPDH expression is quantified by real time PCR, by being run simultaneously with the target, multiplexing, or separately. Total RNA is quantified using RIBOGREEN® RNA quantification reagent (Molecular Probes, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to an SOD1 target nucleic acid. Methods for designing real-time PCR probes and primers are well known in the art, and may include the use of software such as PRIMER EXPRESS® Software (Applied Biosystems, Foster City, Calif.). Primers and probes useful for detection of human and rat SOD1 mRNA are described in U.S. application Ser. No. 10/672,866, published as US 2005/0019915, which is herein incorporated by reference in its entirety.

Analysis of Protein Levels

Protein levels of SOD1 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat SOD1 are well known in the art.

EXAMPLE 1

Inhibition of SOD1 mRNA in Rat Brain Following Intracerebroventricular Administration In order to inhibit the gene expression in the central nervous system, antisense oligonucleotides must be delivered directly to the cerebrospinal fluid by, for example, intracerebroventricular (ICV) administration. To evaluate antisense inhibition of SOD1 in the brains of normal rats, SOD1 mRNA levels were measured in rat brain following ICV administration. SOD1 mRNA levels were measured in both rat spinal cord and rat brain following ICV administration of ISIS 146192, an antisense oligonucleotide targeted to SOD1. Administration was performed daily at either 33 µg/day or 50 µg/day for 14 days. ICV administration of ISIS 146192 significantly reduced SOD1 mRNA levels in the spinal cord and right temporal parietal section of the brain. Thus, antisense oligonucleotides that are delivered to the cerebrospinal fluid via ICV administration are able to inhibit the expression of SOD1 in central nervous system tissues that are affected in ALS. Accordingly, an embodiment of the present invention is the delivery of antisense oligonucleotides to the cerebrospinal fluid by way of ICV administration.

EXAMPLE 2

Antisense Inhibition of SOD1 in Human Fibroblasts

The A4V mutation of SOD1 accounts for 50% of SOD1-mediated familial ALS in the United States. Antisense oligonucleotides targeting SOD1 were tested for their ability to inhibit SOD1 expression in fibroblasts isolated from an individual harboring the A4V mutation. ISIS 333611, ISIS 333624 (complementary to nucleotides 440 to 459 of SEQ ID NO: 1), and ISIS 333636 (complementary to nucleobases 452 to 471 of SEQ ID NO: 1) inhibited SOD1 expression in a dose dependent manner when tested at doses of 3, 10, 30, 100, or 300 nM. SOD2 mRNA levels were not affected.

EXAMPLE 3

Slowed Disease Progression in a Rat Model of Familial ALS

Several lines of transgenic mice and rats have been generated and extensively studied as experimental models of familial ALS. For example, transgenic mice have been engineered to express the human G85R SOD1 variant. Transgenic rats expressing the human SOD1 G93A variant develop symptoms similar to ALS and do not survive beyond three to five months after birth. As such, these transgenic rats are useful for the testing of antisense oligonucleotides targeted to SOD1. The presence of the human G93A SOD1 variant causes human SOD1 mRNA to accumulate to levels approximately 5 to 10 times that of endogenous wild-type rat SOD1.

Antisense oligonucleotide was infused into the right lateral ventricle of 65 day old rats expressing the human G93A SOD1 variant at a dose of 100 ug/day for 28 days, using Alzet minipumps. Following the treatment period, RNA was isolated from different regions of the brain, and SOD1 mRNA levels were measured by real-time PCR. Despite the high level of human SOD1 mRNA, ISIS 146145, ISIS 333611, ISIS 333624, and ISIS 333636 were effective at reducing human SOD1 mRNA in different regions of the brain. For example, ISIS 333611 effectively reduced human SOD1 mRNA levels in the right cortex, cervical spinal cord, thoracic spinal cord, and lumbar spinal cord by approximately 69%, 45%, 50%, and 42%, respectively. Human SOD1 protein levels were reduced following treatment with ISIS 333611 by approximately 40% and 35%, respectively, in the right cortex and cervical spinal cord. Reduction of SOD1 protein was greater at one month than at two weeks, reflecting the known long half-life of SOD1 protein.

An additional study was performed to test the effects of antisense inhibition of SOD1 on ALS disease onset in rats expressing the human G93A SOD1 variant. Animals were treated by ICV infusion of 100 ug/day of ISIS 333611 (n=12) for a period of 28 days. Saline-treated (n=11) animals and control oligonucleotide-treated (n=8) animals served as controls. The timing of disease onset, at approximately 95 days of age, was similar in each group. While antisense inhibition of SOD1 did not slow early disease onset, infusion of ISIS 333611 slowed disease progression, extending survival from 122±8 days to 132±7 days. Infusion of the control oligonucleotide had no effect on disease progression.

An embodiment of the present invention is a method of the slowing of disease progression in an individual suffering from familial ALS by delivering to the cerebrospinal fluid an antisense oligonucleotide targeted to SOD1. In other embodiments, the method further comprises extending the survival of an individual suffering from familial ALS. In preferred embodiments, the antisense oligonucleotide is ISIS 333611.

EXAMPLE 4

Distribution of Antisense Oligonucleotides in Primate Tissues

To assess the distribution of antisense oligonucleotides following delivery to the cerebrospinal fluid, ISIS 13920 (an antisense oligonucleotide having a gapped motif) was infused intracerebroventricularly or intrathecally into non-human primates at a dose of 1 mg/day for 14 days. A monoclonal antibody that recognizes oligonucleotides allowed for the immunohistochemical detection of antisense oligonucleotide. Following ICV infusion, ISIS 13920 distributed broadly throughout the central nervous system, with the highest concentrations found in the cortex and the lowest concentrations found in the hypothalamus. Following IT infusion, antisense oligonucleotides was broadly distributed throughout the central nervous system, with the highest concentrations of oligonucleotides found in the tissue adjacent to the site of infusion, the lumbar cord.

Accordingly, an embodiment of the present invention is the delivery of antisense oligonucleotide targeted to SOD1 to the central nervous system, as well as the cerebrospinal fluid, through intracerebroventricular or intrathecal infusion.

EXAMPLE 5

Administration of ISIS 333611 to Individuals Suffering from Familial ALS

The present invention provides methods of slowing disease progression in an individual suffering from familial ALS. Such methods comprise the administration to the cerebrospinal fluid of the individual a pharmaceutical composition comprising ISIS 333611. Delivery of the pharmaceutical composition to the cerebrospinal fluid allows for contact of the antisense oligonucleotide with the cells of central nervous system tissues, including tissues affected by ALS.

Individuals suffering from familial ALS receive a diagnosis of familial ALS from a physician. The physician's assessment includes the El Escorial criteria, genetic testing to verify the presence of a mutation in the SOD1 gene, and a neurological examination.

A Medtronic SyncroMed® II pump is used to deliver a pharmaceutical composition comprising ISIS 333611 to the cerebrospinal fluid of an individual suffering from familial ALS. The pump is surgically implanted per the procedures outlined by the manufacturer. Drug is retained in the reservoir of the pump, and is pumped at a programmed dose into a catheter that is surgically intrathecally implanted.

The reservoir is loaded with a pharmaceutical composition comprising ISIS 333611 in phosphate-buffered saline. The pharmaceutical composition is administered at an amount that yields an infusion of 8 mg to 12 mg of ISIS 333611 into the cerebrospinal fluid. In preferred embodiments, the amount of ISIS 333611 infused is 10 mg. Administration is for a period of at least 28 days.

Disease progression is measured by methods routine in the art and described herein, for example, using the ALSFSR-R, and measurements of $FEV_1$, FVC, and muscle strength. These methods are used by a physician to assess disease state at initiation of treatment, and this assessment serves as a baseline for disease state. Subsequent assessments are performed at regular intervals during the pharmaceutical composition delivery period; these intervals are determined by the physician. Administration of a pharmaceutical composition comprising ISIS 333611 to the CSF of individuals suffering from familial ALS slows the progression of ALS. In one embodiment, the ALSFSR-R score is not reduced relative to the baseline ALSFSR-R score. In another embodiment, $FEV_1$ is not reduced relative to baseline values. In an additional embodiment, FVC is not reduced relative to baseline values. In a further embodiment, muscle strength, such as hand grip strength, is not reduced relative to baseline values.

SEQUENCE LISTING

```
<160> NUMBER OF SEQ ID NOS: 2

<210> SEQ ID NO 1
<211> LENGTH: 874
<212> TYPE: DNA
<213> ORGANISM: H. sapiens

<400> SEQUENCE: 1
```

-continued

```
ctgcagcgtc tggggtttcc gttgcagtcc tcggaaccag gacctcggcg tggcctagcg        60
agttatggcg acgaaggccg tgtgcgtgct gaagggcgac ggcccagtgc agggcatcat       120
caatttcgag cagaaggaaa gtaatggacc agtgaaggtg tggggaagca ttaaaggact       180
gactgaaggc ctgcatggat tccatgttca tgagtttgga gataatacag caggctgtac       240
cagtgcaggt cctcacttta atcctctatc cagaaaacac ggtgggccaa aggatgaaga       300
gaggcatgtt ggagacttgg gcaatgtgac tgctgacaaa gatggtgtgg ccgatgtgtc       360
tattgaagat tctgtgatct cactctcagg agaccattgc atcattggcc gcacactggt       420
ggtccatgaa aaagcagatg acttgggcaa aggtggaaat gaagaaagta caaagacagg       480
aaacgctgga agtcgtttgg cttgtggtgt aattgggatc gcccaataaa cattcccttg       540
gatgtagtct gaggcccctt aactcatctg ttatcctgct agctgtagaa atgtatcctg       600
ataaacatta aacactgtaa tcttaaaagt gtaattgtgt gactttttca gagttgcttt       660
aaagtacctg tagtgagaaa ctgatttatg atcacttgga agatttgtat agttttataa       720
aactcagtta aaatgtctgt ttcaatgacc tgtattttgc cagacttaaa tcacagatgg       780
gtattaaact tgtcagaatt tctttgtcat tcaagcctgt gaataaaaac cctgtatggc       840
acttattatg aggctattaa aagaatccaa attc                                   874
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Antisense Oligonucleotide

<400> SEQUENCE: 2

```
ccgtcgccct tcagcacgca                                                    20
```

What is claimed is:

1. A method of treating amyotrophic lateral sclerosis (ALS) comprising administering to the cerebrospinal fluid of a subject in need thereof a therapeutically or prophylactically effective amount of a composition comprising:
    a modified oligonucleotide consisting of 12 to 30 linked nucleosides having a nucleobase sequence comprising an 8-nucleobase portion of SEQ ID NO: 3, wherein the modified oligonucleotide is specifically hybridizable with SEQ ID NO: 1, and
    a pharmaceutically acceptable diluent or carrier.

2. The method of claim 1, wherein administering is intrathecal administration.

3. The method of claim 1, wherein administering is intraventricular administration.

4. The method of claim 1, wherein at least one intenucleoside linkage is a phosphorothioate internucleoside linkage.

5. The method of claim 1, wherein at least one nucleoside comprises a modified sugar.

6. The method of claim 5, wherein the modified sugar is a 2'-O-methoxyethyl.

7. The method of claim 1, wherein at least one nucleoside comprises a modified nucleobase.

8. The method of claim 7, wherein the modified nucleobase is a 5-methylcytosine.

9. The method of claim 1, wherein the modified oligonucleotide comprises:
    a gap segment consisting of linked deoxynucleosides;
    a 5' wing segment consisting of linked nucleosides;
    a 3' wing segment consisting of linked nucleosides;
    wherein the gap segment is position between the 5' wing segment and the 3' wing segment and wherein each nucleoside of each wing segment comprises a modified sugar.

10. The method of claim 9, wherein the modified oligonucleotide comprises:
    a gap segment consisting often linked deoxynucleosides;
    a 5' wing segment consisting of five linked nucleosides;
    a 3' wing segment consisting of five linked nucleosides;
    wherein the gap segment is position between the 5' wing segment and the 3' wing segment, wherein each nucleoside of each wing segment comprises a 2'-O-methoxyethyl sugar; wherein each cytosine is a 5' methylcytosine, and wherein each internucleoside linkage is a phosphorothioate linkage.

11. A method of treating amyotrophic lateral sclerosis (ALS) comprising administering to the cerebrospinal fluid of a subject in need thereof a therapeutically or prophylactically effective amount of a composition comprising:
    a modified oligonucleotide consisting of 12 to 30 linked nucleosides having a nucleobase sequence comprising an 8-nucleobase portion of SEQ ID NO: 3, wherein the modified oligonucleotide is 100% complementary to SEQ ID NO: 1, and
    a pharmaceutically acceptable diluent or carrier.

12. The method of claim 11, wherein administering is intrathecal administration.

13. The method of claim 11, wherein administering is intraventricular administration.

14. The method of claim 11, wherein at least one intenucleoside linkage is a phosphorothioate intenucleoside linkage.

15. The method of claim 11, wherein at least one nucleoside comprises a modified sugar.

16. The method of claim 15, wherein the modified sugar is a 2'-O-methoxyethyl.

17. The method of claim 11, wherein at least one nucleoside comprises a modified nucleobase.

18. The method of claim 17, wherein the modified nucleobase is a 5-methylcytosine.

19. The method of claim 11, wherein the modified oligonucleotide comprises:

a gap segment consisting of linked deoxynucleosides;
a 5' wing segment consisting of linked nucleosides;
a 3' wing segment consisting of linked nucleosides;
wherein the gap segment is position between the 5' wing segment and the 3' wing segment and wherein each nucleoside of each wing segment comprises a modified sugar.

20. The method of claim 19, wherein the modified oligonucleotide comprises:

a gap segment consisting often linked deoxynucleosides;
a 5' wing segment consisting of five linked nucleosides;
a 3' wing segment consisting of five linked nucleosides;
wherein the gap segment is position between the 5' wing segment and the 3' wing segment, wherein each nucleoside of each wing segment comprises a 2'-O-methoxyethyl sugar; wherein each cytosine is a 5' methylcytosine, and wherein each internucleoside linkage is a phosphorothioate linkage.

* * * * *

UNITED STATES PATENT AND TRADEMARK OFFICE
CERTIFICATE OF CORRECTION

PATENT NO. : 7,622,455 B2  
APPLICATION NO. : 11/526134  
DATED : November 24, 2009  
INVENTOR(S) : C. Frank Bennett et al.

Page 1 of 1

It is certified that error appears in the above-identified patent and that said Letters Patent is hereby corrected as shown below:

Col. 19, Line 38
1) At the end of the sequence listing, insert the following:

<210> 3  
    <211> 20  
    <212> DNA  
    <213> Artificial Sequence

<220>  
    <223> Synthetic Antisense Oligonucleotide

<400> 3  
    gtcgcccttc agcacgcaca                       20

Signed and Sealed this  
Thirteenth Day of March, 2012

David J. Kappos  
*Director of the United States Patent and Trademark Office*

UNITED STATES PATENT AND TRADEMARK OFFICE
Certificate

Patent No. 7,622,455 B2

Patented: November 24, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: C. Frank Bennett, Carlsbad, CA (US); and Susan M. Freier, San Diego, CA (US).

Signed and Sealed this Seventeenth Day of April 2012.

HEATHER CALAMITA
*Supervisory Patent Examiner*
Art Unit 1635
Technology Center 1600